(12) United States Patent
Shimp et al.

(10) Patent No.: US 6,706,067 B2
(45) Date of Patent: Mar. 16, 2004

(54) SPINAL INTERVERTEBRAL IMPLANT AND METHOD OF MAKING

(75) Inventors: Lawrence A. Shimp, Morganville, NJ (US); Steven Annunziato, Monmouth Beach, NJ (US); Erik Martz, Howell, NJ (US); David R. Kaes, Toms River, NJ (US)

(73) Assignee: Osteotech, Inc., Eatontown, NJ (US)

( * ) Notice: Subject to any disclaimer, the term of this patent is extended or adjusted under 35 U.S.C. 154(b) by 193 days.

(21) Appl. No.: 10/008,279

(22) Filed: Nov. 5, 2001

(65) Prior Publication Data

US 2002/0091447 A1 Jul. 11, 2002

Related U.S. Application Data

(63) Continuation-in-part of application No. 09/705,377, filed on Nov. 3, 2000, now abandoned.

(51) Int. Cl.$^7$ .................................................. A61F 2/44
(52) U.S. Cl. ..................................................... 623/17.11
(58) Field of Search ........................... 623/16.11, 17.11, 623/23.51, 23.63

(56) References Cited

U.S. PATENT DOCUMENTS

| 4,950,296 A | 8/1990 | McIntyre |
| 5,314,478 A | 5/1994 | Oka et al. |
| 5,425,772 A | 6/1995 | Brantigan |

(List continued on next page.)

FOREIGN PATENT DOCUMENTS

| WO | WO 97/25941 | 7/1997 |
| WO | WO 98/17209 | 4/1998 |
| WO | WO99/09914 | 3/1999 |
| WO | WO 99/09914 | 3/1999 |
| WO | WO 00/07528 | 2/2000 |
| WO | WO00/24327 | 5/2000 |
| WO | WO 00/24327 | 5/2000 |
| WO | WO 00/40177 | 7/2000 |
| WO | WO 01/70139 | 9/2001 |

OTHER PUBLICATIONS

Salib, Richard M. MD, Graber, Jack MD, *Femoral Cortical Ring Plus Cancellous Dowel: An Alternative in Anterior Lumbar Interbody Fusion*, 1990, Osteotech, Inc.

Simmons, James Walter, *Bone Banking*, Spine Surgery: An Anthology, pp 459–470.

Salib M.D., Richard M. and Graber, M.D., Jack, *Femoral Cortical Ring Plus Cancellous Dowel: An Alternative in Anterior Lumbar Interbody Fusion*, Osteotech, Inc., 1990.

(List continued on next page.)

Primary Examiner—Eduardo C. Robert
(74) Attorney, Agent, or Firm—Carella, Byrne, Bain, Gilfillan, Cecchi et al; Elliot M. Olstein; William Squire

(57) ABSTRACT

A C-shaped or ring shaped implant formed of cortical bone has its C-shaped or inner channel filled with a bone promoting material which is preferably demineralized bone fibers formed as a flexible wet sheet or may be cancellous bone, pressed bone fibers formed from demineralized cortical bone chips soaked in acid, or a flex material formed of demineralized bone growth promoting bone fibers. The discrete bone filler element may be secured by a bonding agent, pins or screws, metal, polymer or bone material. The bone filler material is preferably bonded by filling a section of a long bone medullary cavity with wet bone fibers and then drying the fibers to bond them to the outer bone. A filled bone ring may be sliced to form annular filled sections which are then divided into mirror image C-shaped halves each forming an implant. Flex material of compressed bone fibers may be formed with an opening shaped to receive a cortical bone implant element having a C-shaped channel. The flex material surrounds the cortical bone element and fills its channel. Other embodiments are disclosed.

11 Claims, 9 Drawing Sheets

U.S. PATENT DOCUMENTS

| | | |
|---|---|---|
| 5,443,514 A | 8/1995 | Steffee |
| 5,458,638 A | 10/1995 | Kuslich et al. |
| 5,522,899 A | 6/1996 | Michelson |
| 5,534,028 A | 7/1996 | Bao et al. |
| 5,591,235 A | 1/1997 | Kuslich |
| 5,645,598 A | 7/1997 | Brosnahan, III |
| 5,669,909 A | 9/1997 | Zdeblick et al. |
| 5,716,415 A | 2/1998 | Steffee |
| 5,766,252 A | 6/1998 | Henry et al. |
| 5,769,897 A | 6/1998 | Harle |
| 5,776,199 A | 7/1998 | Michelson |
| 5,785,710 A | 7/1998 | Michelson |
| 5,888,227 A | 3/1999 | Cottle |
| 5,899,939 A | 5/1999 | Boyce et al. |
| 6,090,998 A * | 7/2000 | Grooms et al. ............. 128/898 |
| 6,096,038 A | 8/2000 | Michelson |
| 6,123,731 A | 9/2000 | Boyce et al. |
| 6,270,528 B1 | 8/2001 | McKay |
| 6,294,041 B1 | 9/2001 | Boyce et al. |
| 6,294,187 B1 | 9/2001 | Boyce et al. |
| 6,425,920 B1 | 7/2002 | Hamada |

OTHER PUBLICATIONS

Tan, MBBS MMed. FRCS(Ed), S. B., Kozak, M.D., Jeffrey A., Graham, M.D., Ph.D., J. Michael Graham, *A Modified Technique of Anterior Lumbar Fusion with Femoral Cortical Allograft*, Journal of Orthopaedic Surgical Techniques, vol. 5, No. 3, 1990.

* cited by examiner

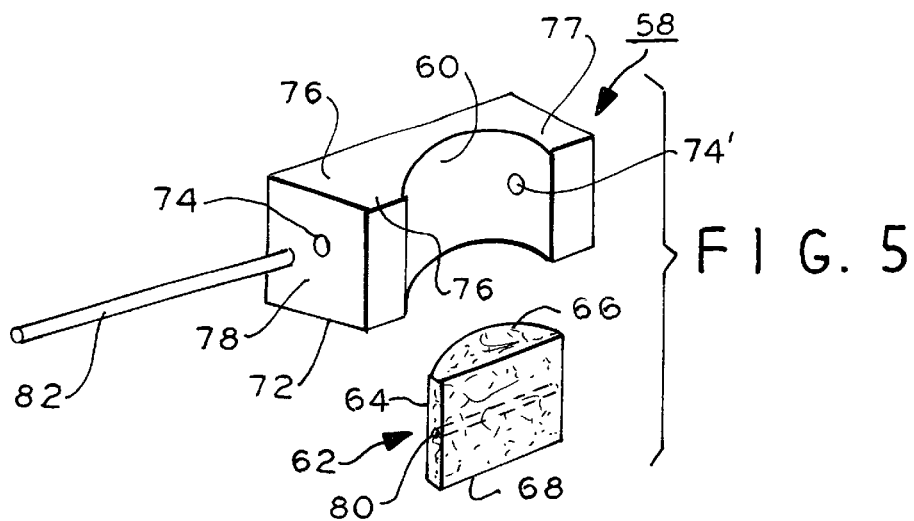
FIG. 5
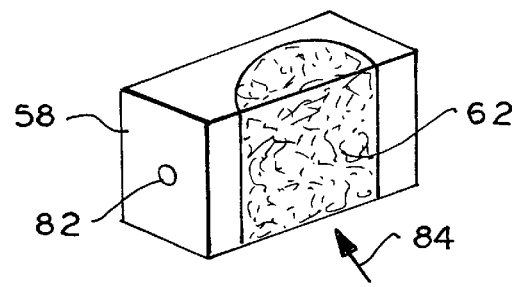
FIG. 6
FIG. 7
FIG. 8
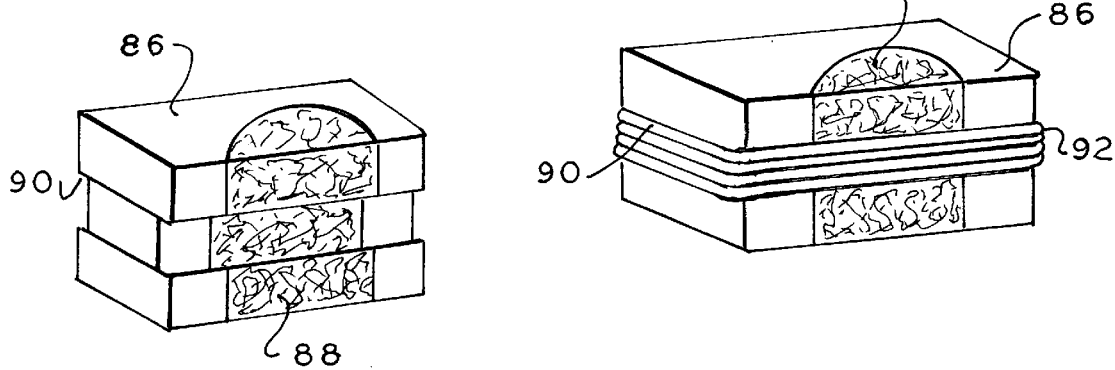

FIG. 9
FIG. 10
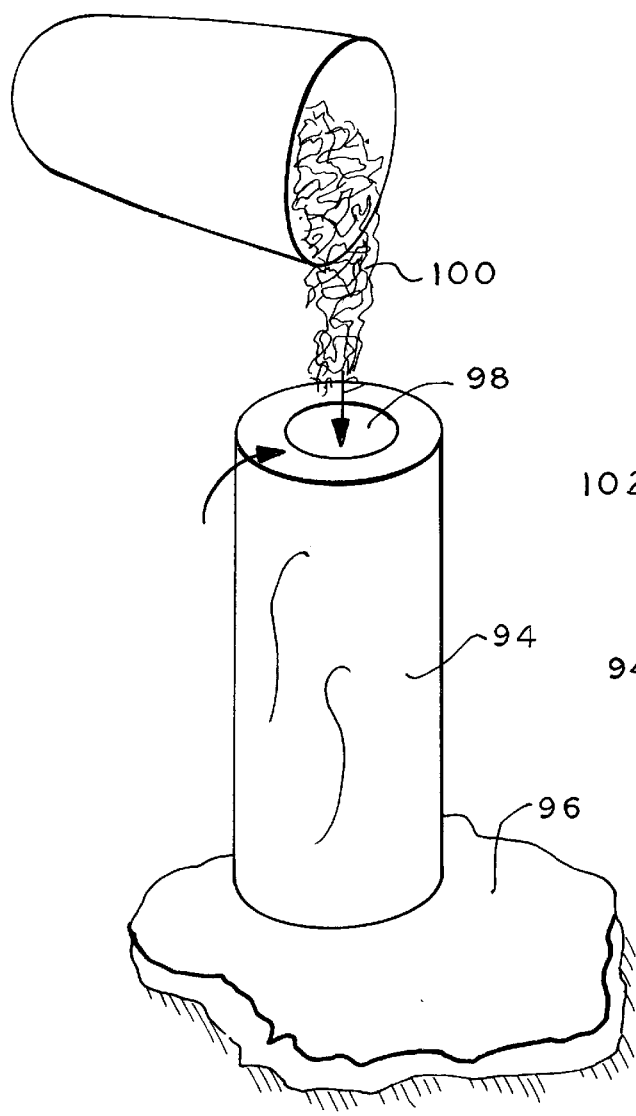
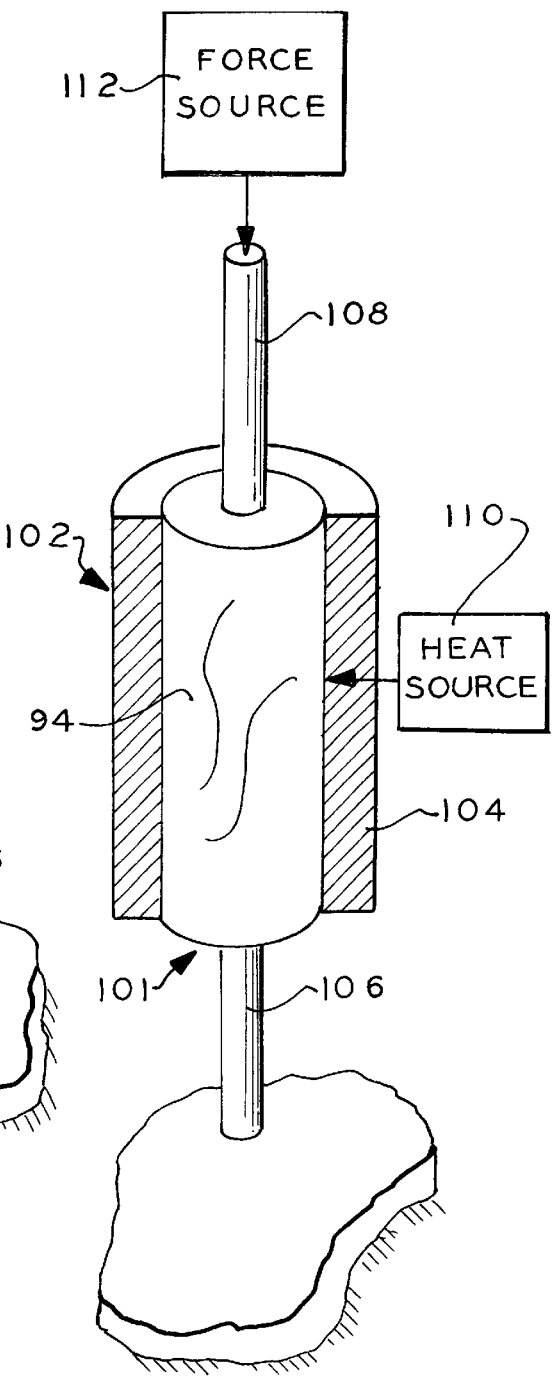

SPINAL INTERVERTEBRAL IMPLANT AND METHOD OF MAKING

This application is a continuation in part of application Ser. No. 09/705,377 filed Nov. 3, 2000 now abandoned.

This invention relates to spinal intervertebral fusion implants and method of making.

Of interest are commonly owned U.S. Pat. Nos. 6,277,149 and 5,507,872.

Surgical procedures for fusing adjacent vertebrae to treat various pathologies are well known. Implants for such procedures take a wide variety of shapes, forms and materials from bone to titanium inert materials, rigid and elastic, circular cylindrical, wedge shapes, cages with or without openings to accept bone fusion promoting material. The implants disclosed in the aforementioned copending applications is preferred. The implants are dimensioned and shaped to provide a predetermined disc space between the fused adjacent vertebra.

Generally, bone growth promoting material is used in conjunction with the implant especially inert implants of metal, ceramic or other synthetic compositions. Often this growth promoting material is in the form of bone chips or bone fibers. These are not normally load bearing materials. Ground up mineralized cortical bone may be used for such chips, but has little bone growth factors. If bone marrow is mixed in the composition, then bone growth factors become present. Such material may be taken from the patient for use in the implant for that patient. The bone source may be the illiac crest of the patient which is not desirable due to pain and long recovery periods.

C-shaped implants are described in Published PCT international applications WO 99/09914 and WO 00/24327 incorporated by reference herein.

U.S. Pat. No. 4,879,915 to Brantigan illustrates a spinal intervertebral implant. The implant is circular cylindrical and has a threaded bore and two opposing radial slots at one end for receiving an insertion tool threaded stud and prongs.

U.S. Pat. No. 4,904,261 to Dove et al. illustrates an inert C-shaped spinal fusion implant.

U.S. Pat. No. 5,192,327 to Brantigan discloses a prosthetic implant for vertebrae.

U.S. Pat. No. 5,443,514 discloses a method for fusing adjacent vertebrae using a spinal implant. The implant has through openings to provide for blood flow and bone growth from one side of the implant to the other side of the implant to adjacent vertebra. The implant is made of chopped fiber reinforced molded polymer, stainless steel or titanium. However, such materials do not permit direct bone in growth into the material and thus is a separate, discrete device which never forms a part of the bony structure of the spine except for the bone in growth in the through openings.

U.S. Pat. No. 5,522,899 to Michlelson discloses spinal implants which are substantially hollow rectangular configurations. In one embodiment, a series of implants are placed side by side in the intervertebral space to substantially fill the disc space. Autogenous bone material is packed within the hollow portion to promote bone growth. In other embodiments a substantially rectangular member has a series of ridges on upper and lower surfaces. The material of the implants is not described.

U.S. Pat. No. 5,7669,897 to Harle discloses a wedge implant having a first component of a synthetic bone material such as a bioceramic material and a second component of a synthetic bone material such as a bioceramic material or bone tissue or containing bone tissue in combination with other biointegration enhancing components. The second material is incorporated in accessible voids such as open cells, pores, bore, holes and/or of the first component. The first component forms a frame or matrix for the second component. The first component imparts strength to the second component. The first and second components can receive one or more pharmaceutical substances. The second component can fully or partially disintegrate upon completion of the implanting to promote penetration of freshly grown bone tissue into the first component.

U.S. Pat. No. 5,716,416 to Lin discloses insertion of an elastic intervertebral implant.

U.S. Pat. No. 5,720,751 discloses spinal insertion tools including a tool with opposing implant engaging portions and including a pusher assembly. In one embodiment the implant engaging portions are fixed and in other embodiments the insertion portion is formed of two arms secured in scissors-like fashion. A pusher may include a threaded stem for attachment to the handle for advancement of the pusher bar toward and away from the implant by rotation of the threaded stem.

U.S. Pat. No. 5,741,253 to Michelson, discloses a threaded self tapping spinal implant and insertion instrumentation. The implant is tubular and cylindrical and is inserted in an opening in the spine formed by a drill inserted in a sleeve.

U.S. Pat. No. 5,443,514 to Steffee discloses an instrument for holding and inserting a spinal implant and which includes an intermediate portion, a handle and a clamp portion. The implant is wedge shaped with two opposing flat parallel surfaces and two inclined surfaces which converge toward one end. The flat surfaces have recesses which receive the clamp of the instrument.

U.S. Pat. No. 5,782,830 to Farris discloses an implant insertion tool somewhat similar to the Steffee disclosure in that a pair of articulating jaws clamp an implant therebetween.

U.S. Pat. Nos. 5,885,299, 5,885,300, 5,910,141, 6,004,326, 6,033,405, 6,042,582 and 6,063,088 illustrate still other insertion tools for a spinal implant.

None of the above patents or applications address or recognize a problem with insertion of a C-shaped ramp or a femoral ring implant. In the C-shaped ramp, a side of the implant is C-shaped and open. During surgery, it is desired to fill the C-shaped opening with fusion promoting material such as bone chips to facilitate bone fusion of the adjacent vertebrae in a posterior insertion procedure. Also during this procedure, two side by side spaced implants may be inserted into the evacuated disc space between two adjacent vertebra. A small opening may be made on one posterior side of the spinal region.

As known, it is desired to fill the space around the implants with fusion promoting material such as bone chips and so on. However to fill the open space after the implants are inserted may be difficult. Even in those procedures where two openings are provided on each side of the spinal cord for separate implants in the posterior approach, a problem of filling the space with bone growth promoting material to promote fusion may be difficult due to the small space available. None of the above noted patents or applications are directed to this problem or offer a solution. Similar problems are present in ring shaped implants.

Another problem is that the C-shaped implant may break at the thinnest section upon insertion.

The present invention is a recognition of these problems and is directed to provide a solution.

A method of forming a fusion implant according to the present invention comprises forming a cortical bone into a discrete bone element having first and second opposing surfaces with a channel in communication with the opposing surfaces; forming a channel filling material of bone fibers; filling the interior channel with the fibers; demineralizing the fibers prior to or after the filling, and then securing the fibers to the discrete bone element. The filled channel thus strengthens the implant for insertion.

Preferably the securing step includes bonding the fibers to the discrete bone element. More preferably, the bonding step includes wetting the fibers prior to or after filling the channel and then drying the wet fibers. This ensures the filled channel retains the fibers without the use of additional elements.

In one aspect, the step of forming the channel filling material of bone fibers includes forming the fibers into a flexible sheet. This simplifies the assembly of the fibers to the implant channel.

In a further aspect, the sheet is formed into a spiral and the spiral is inserted into the channel further facilitating the insertion into the channel.

In a still further aspect, the forming the discrete bone element includes forming cortical bone into a C-shaped structure having a C-shaped cavity forming the channel and in a further aspect, the forming the discrete element includes forming cortical bone into a ring.

Preferably, the step of forming the channel filling material includes forming bone chips and/or powder of cortical bone and demineralizing the chips and/or powder prior to filling the channel.

In a still further aspect, the step of filling the channel includes filling the channel with wetted chips and the step of bonding includes drying the filled implant. The wet demineralized chips form a sticky substance for adhering to the discrete bone element when dried.

In a further aspect, the method includes forming the fibers into a flexible wet sheet, forming the sheet into a configuration generally matching that of the channel, filling the channel with the formed wet sheet and the bonding step includes drying the wet sheet in the channel.

Preferably, the method includes compacting the sheet in the filled implant, and more preferably, compacting the sheet by inserting a pin into the filled implant filling material.

A further aspect includes dividing the ring into two further implants each comprising a first bone element having a chamber open to three adjacent sides of the first bone element, forming the fibers into at least one flexible sheet and filling the chamber with the at least one flexible sheet.

In a still further aspect the step of securing the fibers to the first element includes wrapping the first element and at least one flexible sheet with a filament.

In a further aspect, the step of securing the fibers includes securing the at least one flexible sheet to the first element with a pin.

In a further aspect, the filling the channel step includes forming the fibers into at least one sheet of flexible fibrous material, wetting the fibrous material, wrapping the fibrous wet material about the first discrete element and then drying the wet material to bond it to the discrete bone element.

In a further aspect, a spinal implant for fusing together two adjacent vertebra of a human or an animal according to the present invention comprises a first discrete bone element of a first type of bone having opposing first and second sides extending between first and second end surfaces and a channel in communication with the opposing first and second sides intermediate the end surfaces, the first bone element exhibiting negligible bone growth factors, the bone for implantation between and engaged with adjacent vertebra. A second discrete fibrous bone element is formed of demineralized cortical bone fibers or powder, the second element for promoting bone growth between the adjacent vertebrae, the second bone element having a shape that is complementary to the channel for forming an integral implant unit with the bone of the first type. Means are provided for securing the first element to the second element.

In one aspect, the first element has third and fourth sides transverse the first and second sides, the channel being in communication with the third side to form a chamber open at the third side.

In a further aspect, the means for securing the first element to the second element comprises one of a bonding medium for bonding the elements to each other, a pin and a screw which passes into each element.

In a further aspect, the means for securing the first element to the second element comprises a filament.

In a further aspect, the first element has third and fourth sides transverse the first and second sides, the channel being in communication with the third side to form a chamber open at the third side, the second element forming a portion of the third side, the filament being wound about the end surfaces and the third and fourth sides.

In a further aspect, an annular groove is formed about the elements in the end surfaces and in the third and fourth sides.

Preferably the filament is one of a suture or animal tissue.

More preferably, the means for securing comprises molecular bonding.

In a further aspect, the first bone element has a given peripheral configuration, the second element comprising fibrous flex material having the configuration surrounding and abutting the first element in at least one plane.

IN THE DRAWING

FIG. 5 is an exploded view of an implant according to a further embodiment of the present invention;

FIG. 6 is an isometric view of the implant of FIG. 5 after assembly;

FIG. 7 is an isometric view of an implant in an intermediate stage of assembly according to a second embodiment of the present invention;

FIG. 8 is an isometric view of the implant of FIG. 7 after final assembly;

FIGS. 9, 10 and 11 illustrate intermediate stages of forming an implant according to a further embodiment of the present invention;

Figure 1:
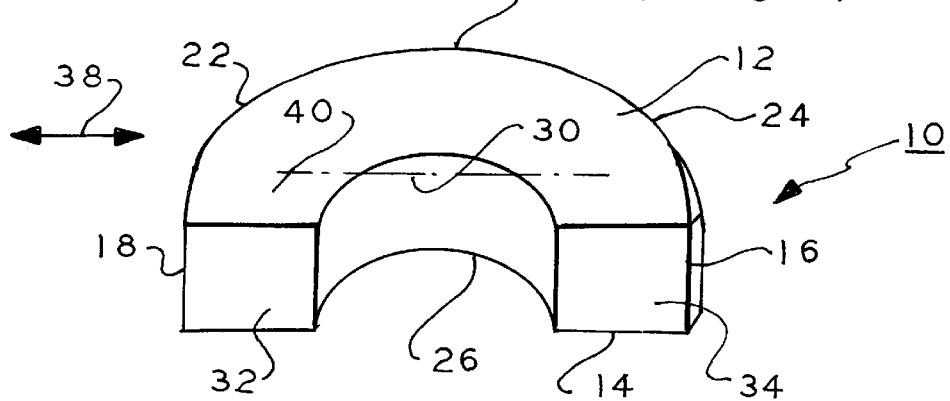
FIG. 1 is an isometric view of a C-shaped spinal implant.
Figure 4:
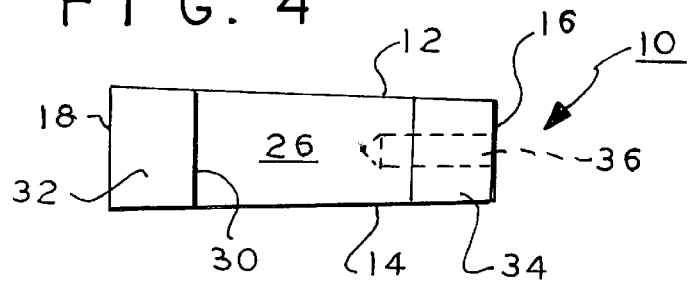
FIG. 4 is a side elevation view of the implant of FIG. 1.

The intervertebral wedge shaped implant 10, FIGS. 1 and 4, which is also referred to as a graft, is made of bone, preferably relatively hard cortical bone, and, in a further embodiment, as described in more detail in the aforementioned U.S. Pat. No. 6,277,149 incorporated by reference herein. The implant 10 has a top surface 12, a bottom surface 14 and two opposite end surfaces 16 and 18. A side surface 20 is centrally flat and terminates in end surfaces 16 and 18 at radii 22 and 24. The implant 10 has a channel 26 which is C-shaped. The channel 26 is formed from the intramedullary canal of a long bone as described in the aforementioned copending application Ser. No. 09/328,242. The channel 26 has a surface 30 that is arcuate and which terminates at side surfaces 32 and 34. The end surface 16 has a threaded bore 36, FIG. 4, in the axial directions 38 of axis 40. The bore 36 receives an insertion tool as described in the aforementioned copending application.

Surfaces 12 and 14 are preferably inclined to form a wedge shaped implant, sometimes referred as a ramp, but also may be rectangular of uniform thickness or curved as in a cylindrical dowel. Surface 16 forms the posterior end and surface 18 forms the anterior end of the implant. The surfaces 32 and 34 are generally coplanar and parallel to the axis 40. Preferably the implant is formed form cadaveric human or animal bone an/or bone composites of sufficient strength comparable to cortical bone to support adjacent vertebra when fused thereto, and more preferably of a long human or animal bone and comprising primarily cortical bone, which is hard and exhibits relatively good strength, but poor bone growth factors.

Preferably, the implant 10 is formed from the cortical ring of a long bone, such as the fibula, ulna, humerous, tibia or femur by cutting the bone transversely across the diaphysis or metaphisis of the bone. This forms a cortical ring. Typically, larger bones are used to form implants for thoracic and lumbar spinal fusion. Smaller bones including the ulna, radius and fibula are used to form implants for cervical spinal fusion. The cut bone is secured and the side walls machined to provide, in one embodiment, a substantially rectangular implant as shown by implant 58, FIG. 5. The side walls are machined to form other configurations such as the preferred taper of the implant 10, FIG. 4, or left in their natural peripheral configuration (not shown). Other shapes may also be provided as desired. The angle of the wedge surfaces 12 and 14, FIG. 4, are arranged to accommodate the inclination of the adjacent vertebrae to maintain the natural curvature of the spine. The various dimensions of the implant are disclosed in the aforementioned patent and copending applications.

Before the long bone is cut, the bone can be partially demineralized by placing it in a 0.6 Normal HCL solution. By demineralizing the bone, only the walls of the intramedullary canal and the circumferential surfaces of the bone are demineralized. With this method, the strength imparting surfaces of the implant will not be compromised. Alternatively, the bone can be partially demineralized after it is cut and machined if it is desired to have a demineralized surface over all parts of the implant. Moreover, the bone may be treated using a variety of bone healing enhancing technologies. For example, bone growth factors may be infused into the natural porosity of the bone and/or the bone may be infused with acid to further demineralize the internal matrix of the bone. These treatments may be performed using the pressure flow system disclosed in U.S. Pat. No. 5,846,484 incorporated by reference herein.

While human bones are preferred, non-human animal bones may also be used.

Figure 2:
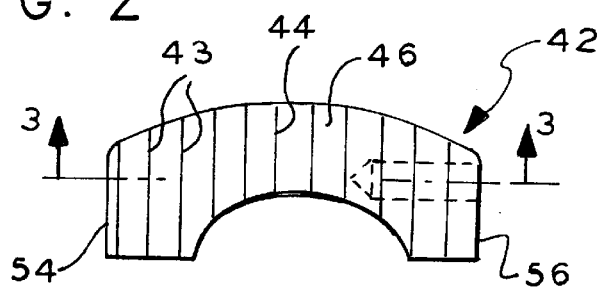
FIG. 2 is a plan view of an implant according to a second embodiment.
Figure 3:
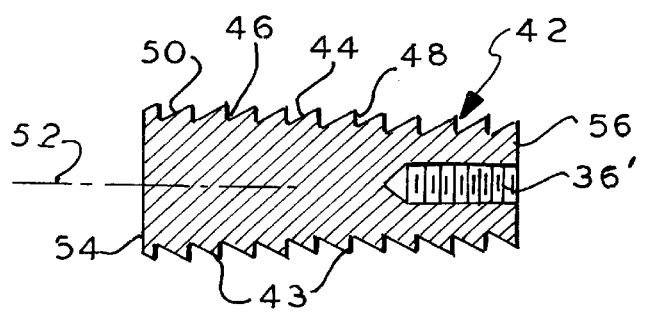
FIG. 3 is a side elevation sectional view of the implant of FIG. 2 taken along lines 3—3.

In FIGS. 2 and 3, in the alternative, implant 42 has the same general shape as the implant 10 of FIGS. 1 and 4, but further includes teeth 43 having ridges 44 spaced by grooves 46. The teeth 43 form saw teeth and have a posterior facing rake 48 and an anterior facing rake 50. Rake 48 is substantially normal to the axis 52 or may be slightly inclined and the rake 50 is inclined toward axis 52. The angle of inclination of rake 50 may be about 45°. The grooves may be about 1 mm in depth for an implant having the dimensions set forth in the aforementioned copending application Ser. No. 09/328,242.

These ridges form serrations in the form of repetitive identical saw teeth 43. The saw teeth 43 have a pitch which is determined for a given implant configuration. The rake surfaces may be both inclined relative to the implant longitudinal axis 52. The teeth 43 serve to prevent withdrawal of the implant after insertion. Surfaces 12 and 14 of implant 10 or the surfaces forming the saw teeth of implant 42 converge at posterior end 16 and 52, respectively to a height in the range of about 7 to 13 mm. The height increases toward the respective anterior ends 18 and 54 in the range of about 9 to 15 mm in one embodiment.

During surgery, anterior end 18 of the implant 10, FIG. 1, or end 54, FIG. 2, of implant 42, is inserted first between the adjacent vertebra in the posterior approach. In this approach normally two incisions are made on opposite sides of the spine for corresponding separate implants. In the alternative, the posterior end may be inserted first in an anterior approach. In the latter case, the threaded bore 36, FIG. 4, will be at end surface 18 or at end 54, FIG. 2.

In FIG. 5, discrete bone element 58, which is of the general peripheral shape as implants 10 and 42 of FIGS. 1 and 2, is shown schematically as rectangular for simplicity of explanation and may be rectangular as shown in certain implementations. The element 58 is formed as discussed above in respect of the implants 10 and 42. The element 58 has a C-shaped channel 60 as discussed above. A second discrete bone element 62 has the same general peripheral shape at surface 64 as the curved interior shape of the channel 60. The upper surface 66 and lower surface 68 of the element 58 are spaced apart a distance so as to be substantially coplanar with respective surfaces 70 and 72 of the element 58. But these surfaces do not have to be coplanar in all embodiments, but is preferred. The element 62 comprises different material than the element 58. The element 62 is preferably bone derived such as demineralized bone fibers including preformed flex sheets formed of fibrous bone discussed below. The element 62 may also be made of materials that are not bone or derived from bone. For example, such materials may include synthetic materials such as ceramics and metals, that never reform into bone, and thus always remain as a separate device. However, one such synthetic material such as titanium can fuse to bone. Also, some synthetic materials may also fuse to bone and eventually reform into bone. Examples are calcium phosphates.

Further, there are other synthetic materials that do not fuse to bone, but are replaced by bone. Calcium sulfate and calcium carbonate are examples. Other materials that may be used include polylactic acid (PLA), polyglycolic acid (PGA), polymethylmethacrylate (PMMA), calcium phosphate cement, bioresorbable polymer among others. Thus a wide range of synthetic materials can be used to fill the implant cavity. The requirements are that they form a mechanical (or chemical) bond to bone, or they can be mechanically fastened to the cortical bone. They are preferably osteoconductive, and either resorb to be replaced by bone, or they contain pores that can be filled with bone. The element 58 is preferably hard cortical bone which does not generally promote bone growth and which provides the desired vertebra support.

The discrete element 62, however, is preferably also formed of bone growth promoting factors and is a solid one piece unitary structure which is received in the channel 60 in close fit. Preferably, the element 62 is formed of bone fibers or chips and then processed to form it into a solid three dimensional unit. As such the element 62 does not exhibit the same strength characteristics of the element 58. Antibiotics and/or growth factors can be incorporated into any filler material such as element 62 that is porous or made of a substance (hydrogel, for example) that can dissolve the antibiotics or growth factors.

The bone chips forming the element 62 may be formed of the illiac crest from the donor bone or from any other desired source. It is preferred that bone fibers be used. Chips from other sources may be used to form active growth factors. Bacteria or DNA techniques may be used to form the bone growth factors in the bone chips or the fibers may be extracted from the bone growth marrow or from animal bones. The element 62 may be formed of porous cancellous bone as it both promotes bone growth and helps support the element 58 as a discrete unitary structure. This structure helps share the load after implantation. It is more porous than cortical bone and permits more rapid bone growth there through.

Demineralized bone fibers are preferred. Cortical bone is ground into chips and formed into fibers by dissolution in HCL solutions. What remains after dissolution are bone fibers of collagen forming a structural protein. Such fibers contain growth factors. Upon dissolution in acid, the fibers become active growth factors and encourage rapid bone growth. In mineralized bone, the growth factors are not active. To form active bone chips cortical bone and bone marrow chips may be mixed and ground together forming a growth factor and chips composite material. This material is formed into a solid discrete element 62 that is shaped to fit in the channel 60, FIG. 5.

A bore 74 is formed in section 76 of the element 58 between the channel 60 and end surface 78. A further bore 74' of the same diameter as bore 74 is formed in section 77. The bores 74, 74' are axially aligned. A third bore 80 is formed in element 62. Bores 74, 74' and 80 aligned with the bores 74, 74' when the element 62 is placed into the channel 60. The bores 74, 74' and 80 preferably are the about same diameter. It should be understood, however, that the threaded bore 36 or 36' (FIGS. 4 and 3, respectively) may be required for insertion for this particular implant and, therefore, the bores 74 and 74' are located accordingly to permit the threaded bore 36, 36' to be employed.

A steel, bone or synthetic material such as a polymer pin 82 is passed into the bores 74 and 80 in preferable friction fit to mechanically secure the element 58 to element 62. The pin 82 is preferably employed when the rigid element 62 comprises cancellous bone, for example. This mechanical joining of the two elements provides enhanced stability to the structure. This ensures a more predictable outcome for the surgery involved. The pin may pass through the threaded bore 36, 36', but the threaded bore 36, 36', must be free to receive the threaded stud of the implant insertion tool. The pin 82 may be parallel to or inclined to the threaded bores. The pin 82 friction fit engages the corresponding bores 74, 74' to retain the second filler element in the channel.

In the alternative, the channel 60 surface may be machined with interlocking surface features that enhance bonding of the element 58 thereto without the pin 82. The fibers of the filler material element fill the surface features under heat and pressure in one embodiment. The interlocking surface features may be grooves, holes or other forms of surface roughness and the like forming a surface roughness in the channel 60 walls.

In an alternative embodiment, FIGS. 7 and 8, cortical bone element 86 of the general C-shape of the element 58, FIG. 5 without the bore 74 is formed. The second element 88 corresponding to element 62, FIG. 5 without the bore 80 is formed. The elements 86 and 88 are then assembled in a mechanical fixture (not shown) and an annular groove 90 is formed about the two assembled elements. The groove 90 is shown rectangular in cross section, but may also be curved or any convenient desired shape for the purpose to be described. In FIG. 8, the groove 90 is filled with a filament 92 wound about the two elements 86 and 88. The filament 92 may be a suture of conventional common absorbable or non-absorbable material, resorbable being preferred, or a thread derived from tissue such as demineralized bone fibers or tendons and the like.

In alternative procedure, in diagrammatic FIG. 9, a portion of a long bone 94 is mounted on a support 96 which blocks the lower entrance of the medullary canal 98 which has previously been emptied of the bone marrow by conventional techniques. The medullary canal 98 inner surface is demineralized and the canal 98 is filled with preferably demineralized bone fibers 100 forming an assembly. In FIG. 10, the bone 94 and filled canal 98 assembly 101 are affixed to a fixture 102. The fixture 102 comprises an outer jacket 104, preferably metal, more preferably stainless steel, or suitable material. The jacket reinforces the bone 94 during the process. The fixture 102 includes two metal rods 106 and 108 which are closely received in the medullary canal 98 (FIG. 9). The length and dimensions of the rods are determined empirically to fit a given canal which may vary from bone to bone. For example, the rods 106 and 108 may be provided in sets of different diameters. The rods are held to the fixture by apparatus (not shown), the diagram being schematic.

A source of heat 110 is coupled to the jacket 104 to heat the jacket to a desired temperature, e.g., 10 to 100° C. and preferably 40 to 45° C., for bonding the bone chips 100 to the surface of the medullary canal 98.

Pressure, from source 112, e.g., 5000 to 30000 psi and preferably 10000 to 20000 psi, accompanied with the heat from the jacket 104 applied by source 110, is applied axially to the filler fiber material by compressing the rod 108 against the bone fibers in the canal and against the rod 106. This pressure and heat causes the filler bone fibers 100 to press against the walls of the channel such as in direction 84, FIG. 6, for example. This heat-pressure action causes a bond between the filler bone fibers and bone 94. The jacket 104 is arranged to withstand the pressure to protect the bone during the process. In the alternative, other methods of filling the channel with demineralized bone fibers is discussed below employing what is known as flex sheets formed of bone fibers and demineralized as discussed in more detail below. The sheets are wetted when in the channel to form a bond to the implant channel receiving the filler material in a process described below.

Figure 11:
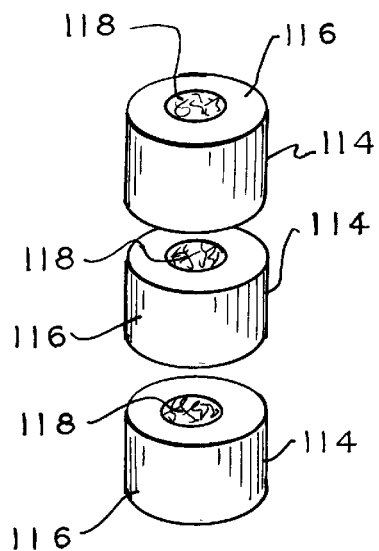

In FIG. 11, the bone 94 and filled medullary canal 98, are transversely cut to form intermediate stage grafts 114. The grafts 114 comprise cortical bone element 116 in an annular form and a central separate discrete bone growth promoting element 118 filling the canal. Each graft 114 is then sliced in half to form the final implant 120 with bone element 114' and canal filling element 118'.

Figure 13:
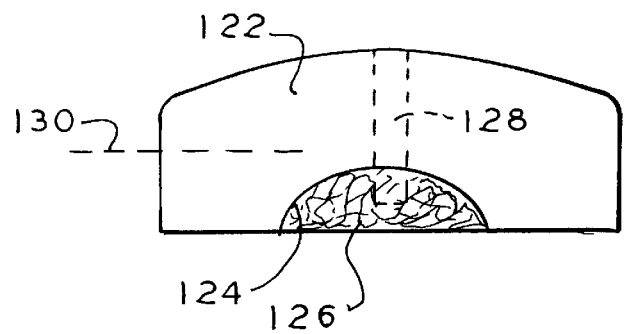
FIG. 13 is a top plan view of the implant according to a further embodiment.

In FIG. 13, in the alternative to the embodiment of FIG. 6, cortical bone element 122 has a channel 124 as described filled with fibrous or cancellous element 126. The element 126 is attached to element 122 by a pin 128. In this case, the pin 128 passes centrally of the element 122 transversely the longitudinal axis 130. Pin 128 may comprise materials discussed above in connection with the embodiment of FIG. 6. The pin 128 passes through the element 122 and partially into the element 126.

Figure 14:
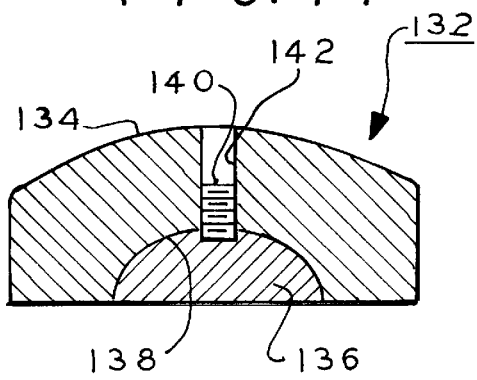
FIG. 14 is a top plan view of an implant according to a still further embodiment.
Figure 15:
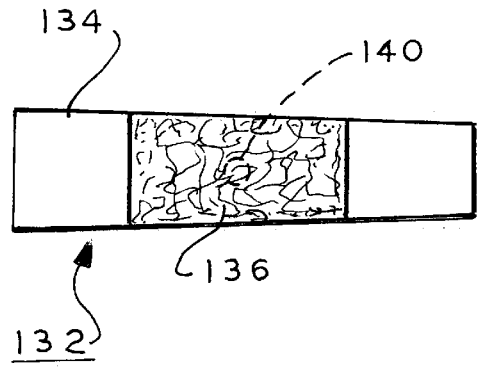
FIG. 15 is a side elevation view of the implant of FIG. 14.

In FIGS. 14 and 15, in a further embodiment, implant 132 comprises a first bone element 134 formed from a bone as described above in the other embodiments and a second element 136 fills the medullary canal formed channel 138 in the bone element 134. A screw 140, which may be metal or a polymer, fits partially in a bore 142 in the element 134. The element 136 may be formed as described above in connection with FIGS. 5–6, e.g., cancellous bone with bone growth promoting factors. The screw 140 is inserted partially into the element 136 whose bore extends partially into the element to optimize the integrity of the element 136.

Figure 12:
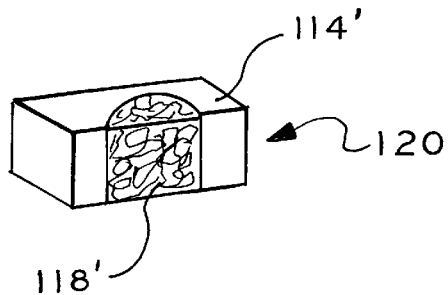
FIG. 12 is an isometric view of the implant of a third embodiment formed by the processes illustrated in FIGS. 9–11.
Figure 17:
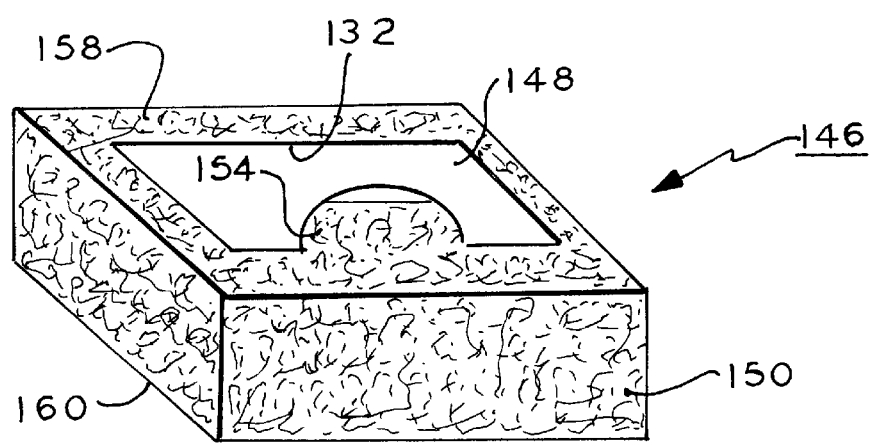
FIG. 17 is an isometric view of the implant of FIG. 16 after assembly.

In FIG. 17, a further alternative embodiment comprises an implant 146 having a first bone element 148 and a second element 150. The first element is fabricated as described above for the element 58 of FIG. 5, but without the bores 74, 74'. In the alternative the element 148 may be fabricated as shown in FIGS. 11 and 12, but with an empty medullary canal. The element 148 is as described above in connection with the implant 10 of FIG. 1 or implant 42 of FIG. 2, for example.

Figure 16:
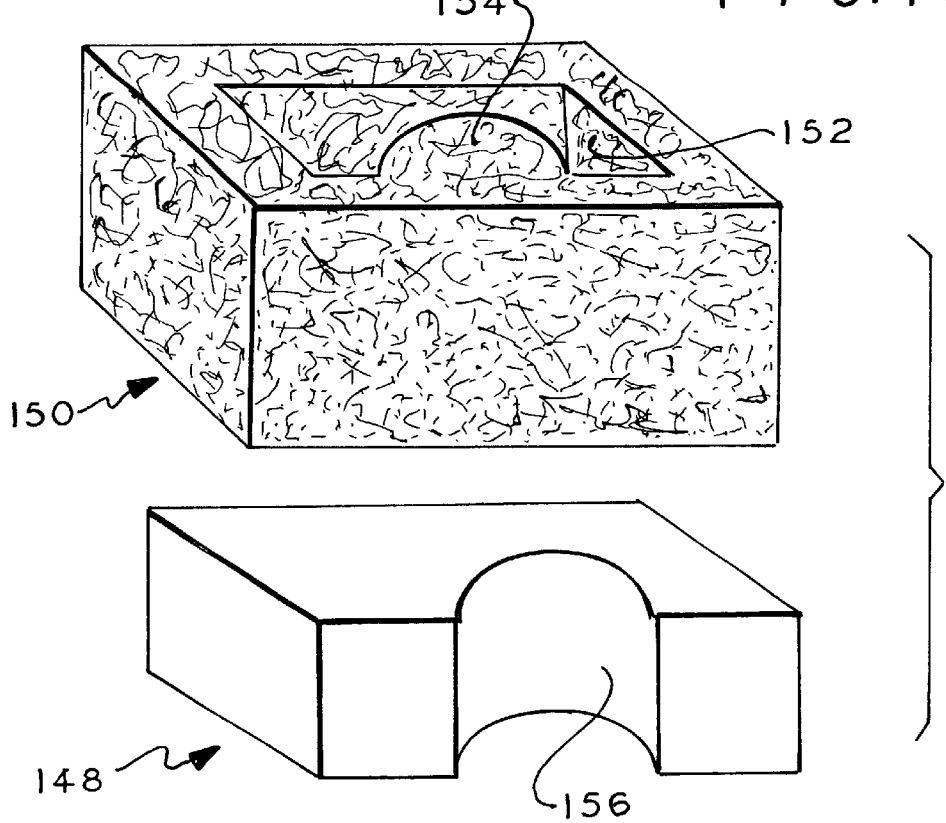
FIG. 16 is an exploded isometric view of an implant at an intermediate stage of assembly in a further embodiment of the present invention.

The second element 150, FIG. 16, comprises what is termed in this art as a flex material. This flex material is commercially available in flat strips. The strips are flexible. The flex strip comprises demineralized bone fibers with the demineralization activating the naturally contained bone growth factors. It is available as an integral discrete structure. The strip is available, for example, in 2 cm×10 cm×4 mm thickness. It is also available in other sizes. Also the material is available in different densities. The bone fibers are formed of demineralized cortical bone. These fibers are compressed to form the strip.

The strip is then shaped to form the element 150, FIG. 16. The strip has a central opening 152 shaped to closely receive the element 148. The strip has a projection 154 that is complementary to the medullary canal channel 156 in the element 148. The element 150 completely surrounds the element 148 enclosing the element 148 in a plane. Both elements are exposed on opposite sides 158 and 160. The flex material provides little structural support to the assembly and serves to promote bone fusion when inserted between adjacent vertebra.

As known, cancellous bone is porous, and when used as the filler element for the implant embodiments described, it promotes bone growth there through. The bone fibers and bone chips and cancellous bone filler materials for the medullary channel of the implant elements are all bone promoting materials and eventually form permanent bone structure fused to the vertebra. In contrast, synthetic materials such as ceramics and metals, never reform into bone, and thus always remain as a separate device. However, one such synthetic material such as titanium can fuse to bone. Also, some synthetic materials may also fuse to bone and eventually reform into bone. Examples are calcium phosphates. Further, there are other synthetic materials that do not fuse to bone, but are replaced by bone. Calcium sulfate and calcium carbonate are examples. Other materials that may be used include polylactic acid (PLA), polyglycolic acid (PGA), polymethylmethacrylate (PMMA), calcium phosphate cement, bioresorbable polymer among others. Thus a wide range of synthetic materials can be used to fill the implant cavity. The requirements are that they form a mechanical (or chemical) bond to bone, or they can be mechanically fastened to the cortical bone. They are preferably osteoconductive, and either resorb to be replaced by bone, or they contain pores that can be filled with bone.

The fusion takes place with the bone growth material placed adjacent to these devices and such synthetic materials for implants may not in all cases be as desirable as implants made only of bone. While metal pins and screws do not permanently form bone tissue and remain separate devices, they are held in place by the surrounding bone which, in the case of two different bone element materials, eventually forms into a single fused bone structure in the implanted device. Cancellous channel bone filler material is preferred because it can form a load bearing structure as compared to fibrous materials. Additional load bearing structures are preferable and should be used where possible. The mechanical connection of the filler material in the channel ensures proper placement of the secondary element in the filled channel. Eventually the different discrete elements bond in place after implantation due to ingrowth and/or remodeling by surrounding living bone. The flex material, because it is demineralized cortical bone fibers, can bond to the cortical bone element before implantation, or, depending on how it is inserted and treated after insertion in the cortical element, it may be held in place only by friction until the composite unit is implanted. If the filler material is chemically bonded to the cortical element, it can help to reinforce the cortical element against the forces of surgical implantation. This is true even if the filler exhibits no long term load bearing ability. For example, the flex type of demineralized filler is hard and strong when dry (before implantation), but swells and weakens in contact with fluids (after implantation).

In further embodiments, the channel filling element may be bonded by chemical binders such as a biocompatible glue or polymer. The secondary filler bone growth promoting element may be ceramic, preferably porous, or a polymer material, also porous. The filler material could in another embodiment be used to increase the width of the implant or its length as well as fill the channel for those implants having such channels. The secondary element material, for use with primary non-bone growth promoting bone elements such as cortical bone elements, which have no channels, is a bone growth promoting material having a shape and configuration which may be added to one or more sides of the primary element by bonding or securing by arrangements discussed above. Such implants are not devices in the sense that they eventually reform and fuse as an integral one piece bone that is not distinguishable from the composition of the vertebra bone being fused. Metal or other non-bone compositions such as polymers never reform as bones and rely solely on the adjacent bone growth material to maintain the integrity of the fused joint. This latter arrangement is not as satisfactory as the former arrangements.

Figure 18:
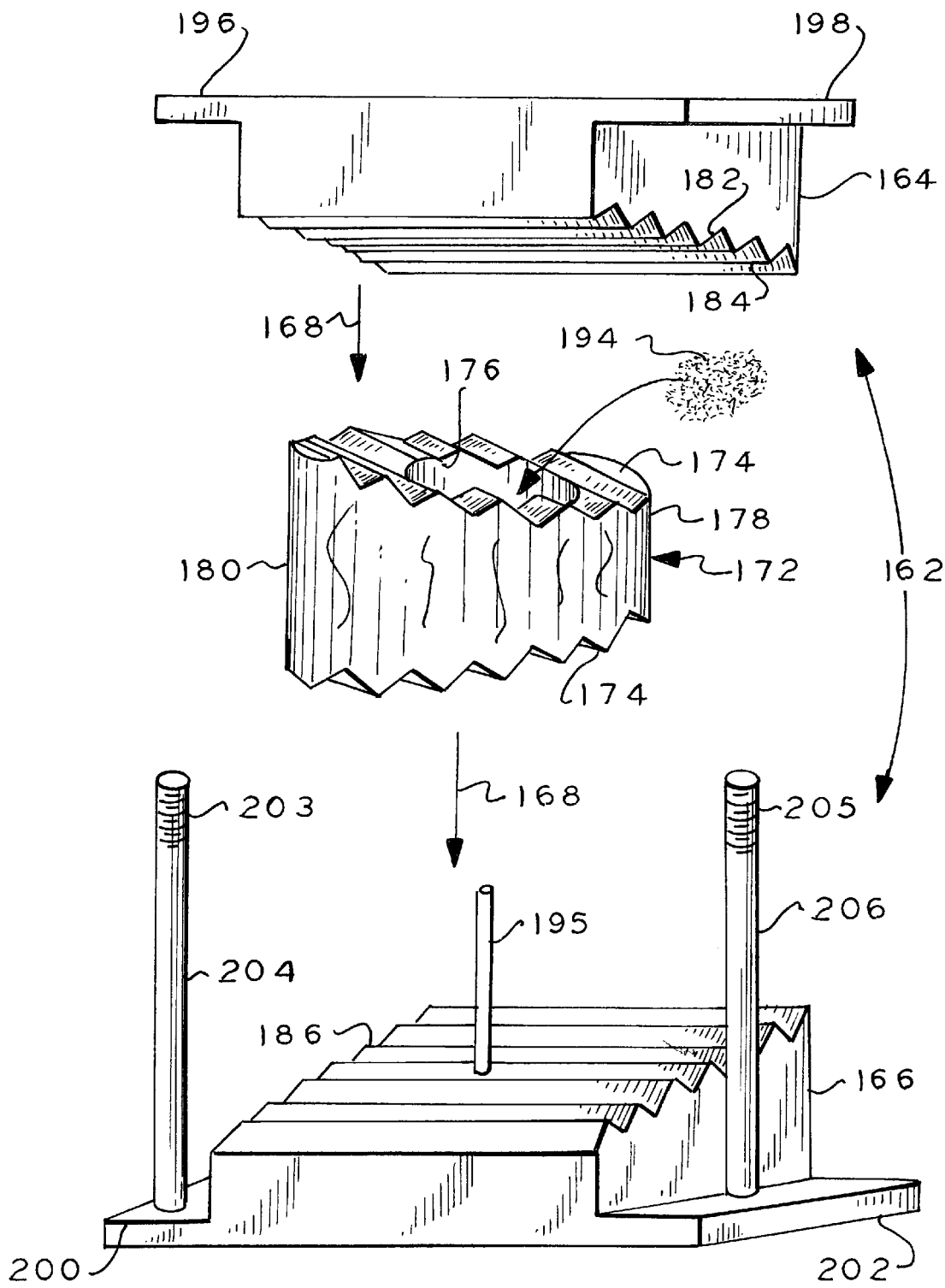
FIGS. 18 and 19 are respective exploded and assembled isometric views of an apparatus and implant according to a further embodiment.
Figure 19:
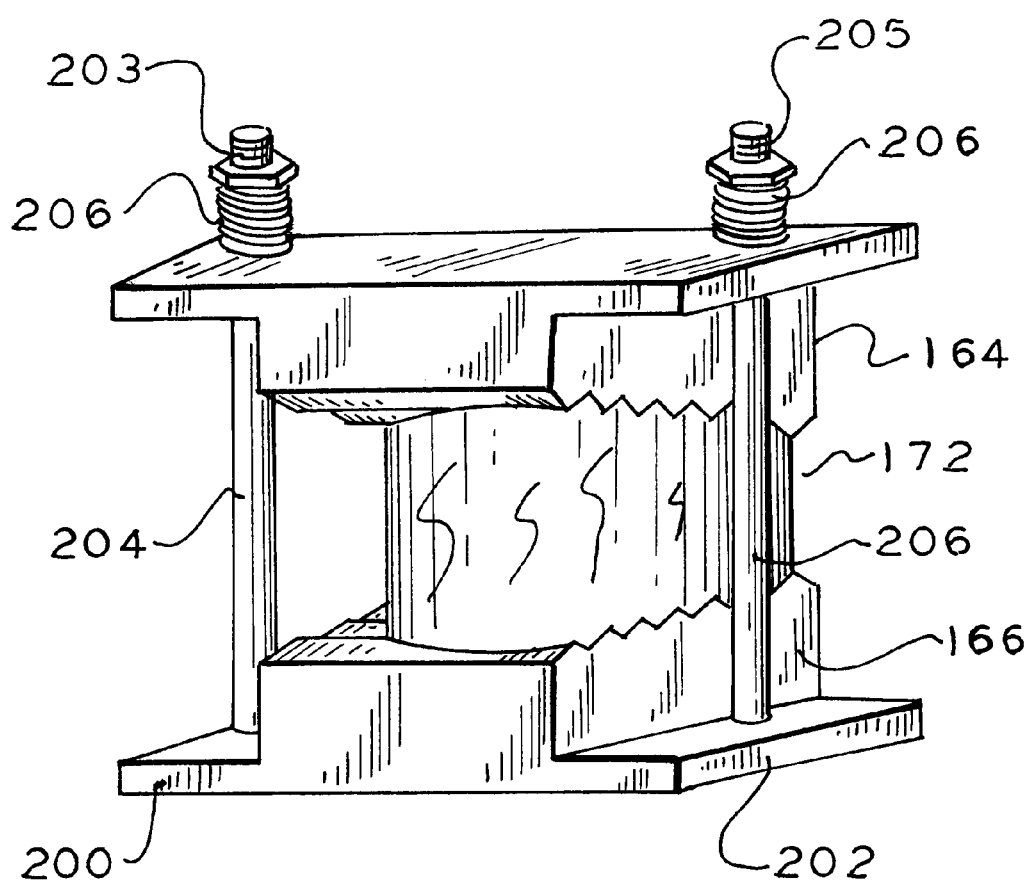

In FIGS. 18 and 19, a mold 162 comprises a metal upper die 164 and a metal complementary lower die 166. Die 164 is manually displaced in translation toward lower died 166 in direction 168, while the lower die 166 is held stationary.

A cortical bone ring 172 is formed by transverse cuts through the long bone as known in this art. The ring 172 is cleaned and processed also in a known manner to remove contaminants. The ring can be surface demineralized prior to filling its bore as described below. Vertebrae gripping teeth 174 are formed on top and bottom surfaces of the ring 172. The teeth may be in the shape of saw teeth in linear arrays on the ring surfaces, or any other shape as desired, the teeth on the top and bottom surfaces being identical and parallel to each other, for example. The ring 172 is formed with a central bore 176 generally corresponding to the medullary canal. The bore 176 is machined into a circular cylinder. The top and bottom surfaces taper toward each other and toward the posterior end 178 from the anterior end 180 which is the widest portion and the posterior end the narrowest, in a known manner to accommodate the lordosis of the vertebrae to which the implant is to fuse.

The upper die 164 has a tapered surface 182 with teeth 184 on its lower surface which mate with the tapered top surface teeth 174 of the ring 172. The die 164 has two outwardly extending flanges 196, 198, each with a through aperture for receiving a corresponding rod 204 and 206.

The lower die 166 has a toothed surface 186 with teeth that mate with and receive the teeth 174 of the ring 172 bottom surface. The lower die has two flanges 200 and 202 extending outwardly therefrom. Flange 200 has a rod 204 extending upwardly therefrom and flange 202 has a rod 206 extending upwardly therefrom. The rods 204 and 206 have threads 203 and 205 respectively, which pass through the apertures in the flanges 196 and 198. The lower die can optionally include a pin 195 extending upwardly therefrom aligned with the bore 176 of the ring to pass through the bore 176 to form a hole in the filled bone growth promoting material in the bore 176.

The demineralized bone chips or powder are prepared similarly as commercially available flex sheets formed of bone chips or fibers, but not pressed into a sheet. The bone powder or chips are fully or partially demineralized in acid or a mixture of the two forms of bone. After the acid is drained, optionally the powder or chips may be rinsed. Excessive liquid may be removed by clotting, vacuum filtration, centrifugation and so on. A base such as sodium hydroxide may be used to neutralize the bone powder or fibers, especially if rinsing is not carried out. The bone chips or powder may be further dried by rinsing with anhydrous alcohol or by lyophilization (freeze drying), or by oven drying with or without a vacuum.

In operation, the bone ring 172 is manually placed onto the lower die 166 as shown in FIG. 18, direction 168, with the teeth of the lower die 166 engaged with the teeth of the ring 172 bottom surface. Powdered demineralized bone or demineralized bone fibers or chips 194 are then placed in the bore 176 of the ring. 172. The powder or chips are wetted prior to being packed into the ring 172. A water/alcohol solution, water, acid or a base can be used for wetting the powder or chips. If the bone ring 172 is not surface demineralized, it is preferable to wet the powder or chips 194 with acid. It is preferred that the ring 172 be fully machined on all surfaces to reduce the chances of disturbing the filler chips after being placed in the bore 176.

The chips 194 are hand packed into the ring bore 176, and then the upper die 164 is placed as shown in FIG. 19. The optional pin 195 (FIG. 18) passes through the bone chips to provide a through hole in the powder and/or filling material.

The upper die 164 is clamped in place against the top surface of the ring 172 by springs 206, FIG. 19, and nuts 203 and 205. The clamping arrangement is given by way of illustration and may be implemented by other clamp mechanisms (not shown). The clamped implant assembly is then dried by any suitable process such as with a vacuum oven, lyophilizer, convection oven and so on. After drying, the mold is opened and the finished implant is removed and further machined if necessary. This drying process results in a bonding between the filled chips and/or powder with the outer cortical bone ring without further mechanical attachment devices and without heat and pressure.

Figure 20:
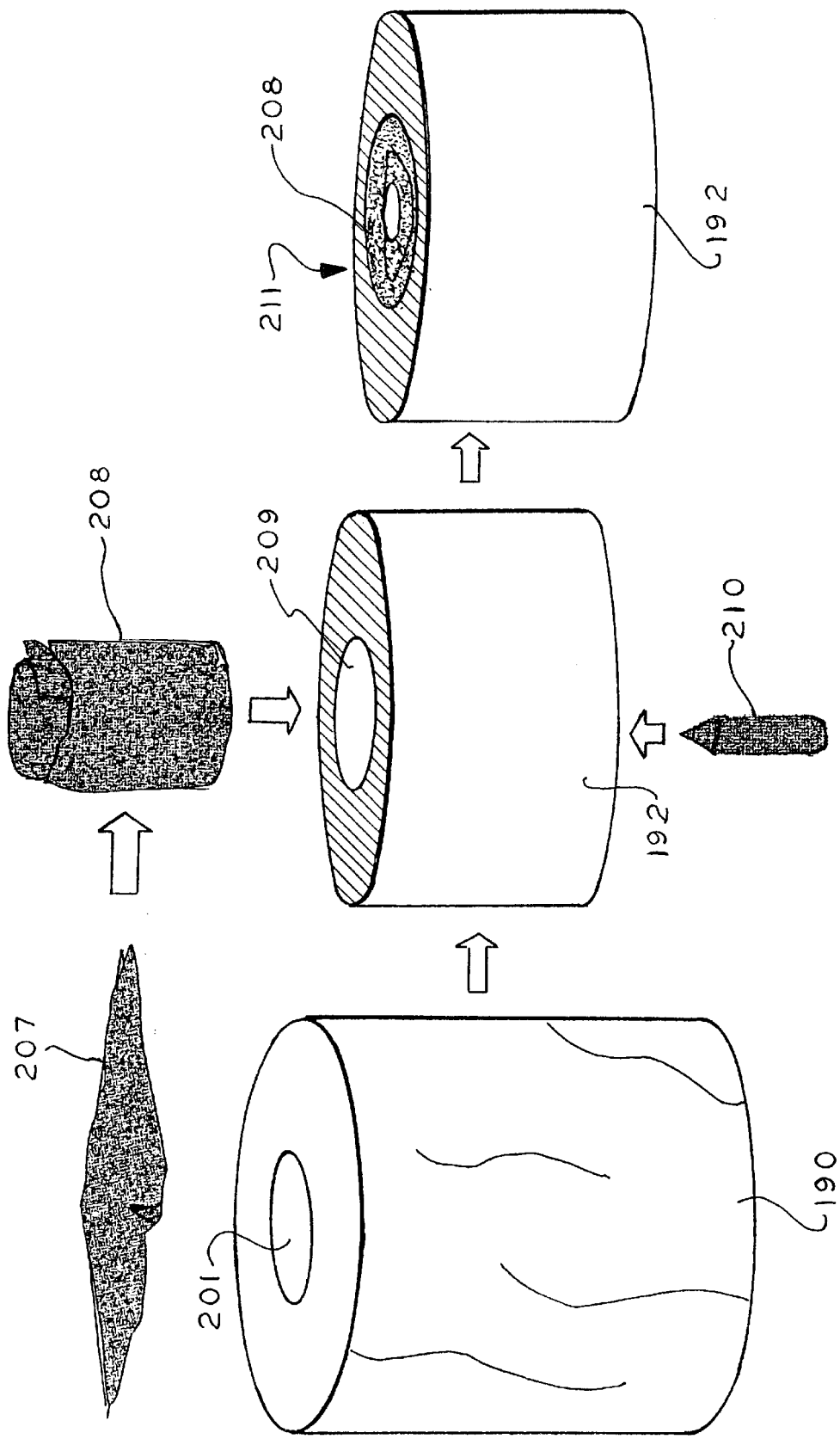
FIGS. 20 and 21 are schematic diagrams of processes for filling the channel of a ring implant with flex bone fibrous material for promoting bone growth.

In FIG. 20, a further embodiment shows a long bone 190 which is cut into a ring 192. The ring 192 may be cut from a femur bone and is machined into an implant shape which may include a lordotic angle between opposite top and bottom surfaces, textured load bearing surfaces for abutting the adjacent vertebrae being supported and/or fused by the implant, instrument interface surface features for receiving an insertion tool for example, specific overall outer dimensions, or in the alternative, left merely as a femoral ring. The ring 190 has a central bore 201 to be filled with bone growth promoting material in the form of a flex sheet 207 comprising material formed of bone chips and which is flexible. The ring may be partially demineralized (surface demineralized). The composite bone material sheet 207 preferably is made of fibers, or less preferably, of particles, and is at least partially demineralized and preferably fully demineralized.

The largest donor bone, the femur, is used to make the rings while smaller donor bones are used for making the filler fibers. The fibers are milled from a small bone shaft using conventional processes using a milling bit passing over a mineralized bone shaft. The fibers are then passed over a 500 micron screen sieve optionally to remove smaller pieces. Optionally the fibers may be defatted.

Defatting includes washing the bone with a fat solvent which may include organic material such as alcohol (isopropanol or ethanol, for example) or stronger solvents such as a mixture of chloroform and methanol, or water based solutions containing surfactants suitable for lipid solubilization as disclosed in U.S. Pat. Nos. 5,820,581, 5,797,871, and 5,556,379 or by enzymes that attack and solubilize fat (lipases) as shown in U.S. Pat. No. 6,037,451. After defatting, the fibers are demineralized.

The flex sheet 207 may be formed as shown in U.S. Pat. No. 5,507,872. The sheet 207 may be formed as a variation of the disclosed process by using two demineralization treatments with a large excess of 0.6 Normal HCL. A single demineralization forms a partially demineralized material. However, the demineralized fibers are not rinsed and no glycerol is added to keep all dissolved liquids in the fiber mix to assist in bonding of the fibers to hold the filler material together and to the cortical bone ring receiving the mix. Instead of rinsing, the material is neutralized with NaOH (pH 6.5 to 7.5) after the fibers have been put into a flexible sheet format forming a cassette and drained. The sheet is lyophilized employing a conventional procedure for this process, while retaining the liquids as much as possible for adhering the fibers together to form a bonded structure.

In the alternative, the material may be partially demineralized by using less acid or water diluted acid and so on. The sheet 207 is rolled into a compact spiral 208.

The implant is formed using conventional fabrication processes including reaming the medullary canal prior to making the transverse cuts forming the ring to alter the natural architecture of the medullary canal. The ring is surface demineralized by soaking in a 0.6 Normal HCL bath for about an hour, just prior to filling the bored canal with the spiral 208 of flex material. Preferably, the ring is not dried or rinsed after removal from the acid bath, permitting the ring to just drain.

Bone contains about 70 weight per cent calcium phosphate mineral in the form of apatite. Acid is used to dissolve the mineral from the bone. Any acid can be used, but HCL is normally used. However, diffusion of the acid through the bone slows the process so it is desirable to maintain a large excess of acid to drive the process. Thus, more acid is added than is needed to chemically dissolve the calcium phosphate. The degree of demineralization depends on acid concentration and time. By limiting one or both factors, the demineralization process can be stopped before completion. U.S. Pat. Nos. 6,189,537 and 6,305,379 disclose controlling demineralization to a 1% to 4% calcium level because this is asserted therein to give optimum biological performance.

A further variation is to cut a small cortical bone shaft so that it will fit approximately in the canal of a larger bone ring, then demineralize the small shaft section (preserving the liquids as with other forms of demineralized bone), then insert the demineralized ring into the larger bone section (preferably using a tapered pin inserted into the smaller bone to force it in place) and then drying the implant as in the other described constructs.

Figure 21:
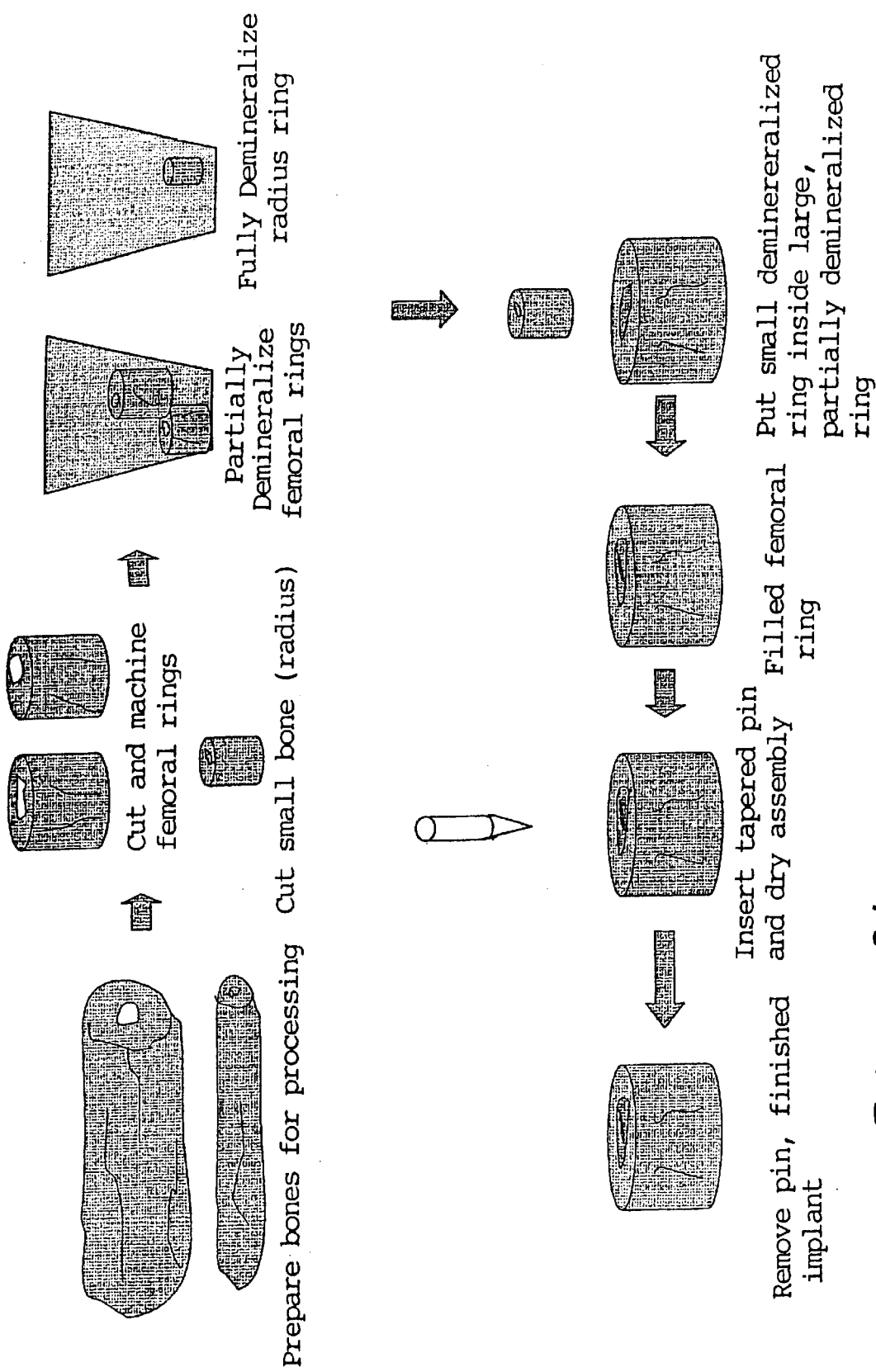

This forms the flex filling process except that the flex sheet is preformed as a demineralized bone ring. This process is shown in FIG. 21. One variation is that the small ring can be partially demineralized. Another variation is that the larger femoral ring can be surface demineralized after the smaller ring is inserted inside its bore. The tapered pin is optional. In a further alternative, the center of the larger ring is filled with another mineralized, demineralized, or partially demineralized piece of cortical bone that has been cut to fit. This bone piece can be formed from any source that is sufficiently large to fit in the larger ring bore, such as the cortical bone wall of another bone such as the tibia. In a further alternative, the filled ring can be machined after it is dried.

Optionally, the ring canal is machined smooth so as to increase the surface area in contact with the spiral 208 and the ring is defatted prior to demineralization. Also, optionally the ring surface may not be demineralized. It is not recommended to machine the ring after filling with the flex material as the dried ring may be damaged by such machining.

The rolled up spiral 208 of sheet material preferably of about 2 mm thick is placed in the bore 209 of the ring 192. The spiral material should be wet to make it flexible. Optionally, a center hole can be formed in the inserted spiral 208 by insertion of a tapered pin 210 into the inserted spiral. This forms the final filled ring 211. The pin 210 is preferably about 8 mm in diameter and is forced into the spiral without disturbing the spiral. Optionally, the assembly may be surface demineralized especially if the sheet 207 has not been fully demineralized.

The composite is dried at a temperature of about 60° C. for 2 hours and then vacuumed for about 4 to about 12 hours while maintaining the temperature. Optionally, the composite may be dried at a maximum temperature of 45° C. or lyophilize employing a conventional freeze drying process.

Flex fibers under moderate pressure can form a translucent plastic like sheet. This sheet will eventually swell and rehydrate over a number of hours. Composite sheets that are freeze dried with the neutralized demineralization fluids present have a rich source of potential bonding material present in them. This bonds the flex material in the outer ring bore to the ring. Freeze drying also reduces the sheet thickness, making it easy to compact after placement, since most voids are already removed. Carrying out demineralization in ways that promote a recrystalized, mineralized surface on the bone elements can also help to bond the filler to the ring.

Compacting the sheets with the tapered pin 210 achieves 30 to 50% compaction of the sheets at the same time a center hole 211 is formed. As the ring shrinks upon drying, it further compresses the composite spiral 208 which shrinks somewhat by itself because it is minimally hydrated at the fabrication step. The net result is believed to be a stronger composite with bonding to the cortical ring 192.

It should be understood that the term channel in the claims includes bores, canals or openings forming a hollow space. Further, rings include end surfaces wherein one end corresponds to an anterior site in a bone of a patient being fused and/or supported by the implant and the other end corresponds to a posterior site in a bone of a patient being fused and/or supported by the implant. Rings may be defined as having a longitudinal direction corresponding to the anterior/posterior direction of the implant. The anterior/posterior direction of an implant corresponds to the anterior/posterior position of the inserted implant in the site of a patient exhibiting such anterior/posterior locations.

The term fibrous as used in the claims includes fibers, powder and chips formed of bone. The term demineralized as used in the claims includes both full demineralization and partial demineralization.

It will occur to one of ordinary skill that modifications may be made to the disclosed embodiments without departing from the scope of the invention as defined in the appended claims. The disclosed embodiments are given by way of illustration and not limitation. For example, while flex material is disclosed completely surrounding the cortical bone C-shaped element in one embodiment, it may partially surround the element or be placed on one or more sides of the C-shaped element. It may also be used to just fill the channel or, in the alternative, extend outside the channel to cover the sides of the mating element such as sides 32 and 34 of element 10, FIG. 1, as well as fill the channel 26. In addition, other sides of the element 10 may also be encased by flex material according to a given implementation. The flex material is also formed to fill or partially fill the medullary canal bore of bone rings. The filling material is demineralized or partially demineralized and used with a cortical bone in wet form to form a bonding medium to bond the demineralized bone to the adjacent cortical bone, regardless its shape.

What is claimed is:

1. A spinal implant for fusing together two adjacent vertebra of a human or an animal comprising:
   a first discrete bone element of a first type of bone having opposing first and second sides extending between first and second end surfaces and a channel in communication with the opposing first and second sides intermediate the end surfaces, the first bone element exhibiting negligible bone growth factors, the bone for implantation between and engaged with adjacent vertebra;
   a second discrete fibrous bone element formed of demineralized cortical bone fibers or powder, the second element for promoting bone growth between said adjacent vertebrae, the second bone element having a shape that is complementary to said channel for forming an integral implant unit with said bone of the first type; and means for securing the first element to the second element.

2. The implant of claim 1 wherein the first element has third and fourth sides transverse the first and second sides, the channel being in communication with the third side to form a chamber open at the third side.

3. The implant of claim 1 wherein the means for securing the first element to the second element comprises one of a bonding medium for bonding the elements to each other, a pin and a screw which passes into each said element.

4. The implant of claim 1 wherein the means for securing the first element to the second element comprises a filament.

5. The implant of claim 4 wherein the first element has third and fourth sides transverse the first and second sides, the channel being in communication with the third side to form a chamber open at the third side, the second element forming a portion of said third side, the filament being wound about the end surfaces and said third and fourth sides.

6. The implant of claim 5 wherein an annular groove is formed about said elements in said end surfaces and in said third and fourth sides.

7. The implant of claim 4 wherein said filament is one of a suture or animal tissue.

8. The implant of claim 1 wherein the means for securing comprises molecular bonding.

9. The implant of claim 1 wherein the first bone element has a given peripheral configuration, the second element comprising fibrous flex material having the configuration surrounding and abutting the first element in at least one plane.

10. The implant of claim 9 wherein the implant has a C-shaped channel in communication with three adjacent sides, said second element filling said channel.

11. The implant of claim 10 wherein the second element is sheet material of uniform thickness and extending radially outwardly from the first element in regions outside the channel.

* * * * *